United States Patent
Stensrud et al.

(10) Patent No.: US 9,828,387 B2
(45) Date of Patent: Nov. 28, 2017

(54) CONTROL OF COLOR-BODY FORMATION IN ISOHEXIDE ESTERIFICATION

(71) Applicant: ARCHER DANIELS MIDLAND COMPANY, Decatur, IL (US)

(72) Inventors: Kenneth Stensrud, Decatur, IL (US); Erik Hagberg, Decatur, IL (US); Erin Rockafellow, Decatur, IL (US)

(73) Assignee: Archer Daniels Midland Company, Decatur, IL (US)

( * ) Notice: Subject to any disclaimer, the term of this patent is extended or adjusted under 35 U.S.C. 154(b) by 0 days.

(21) Appl. No.: 15/102,281

(22) PCT Filed: Nov. 19, 2014

(86) PCT No.: PCT/US2014/066301
§ 371 (c)(1),
(2) Date: Jun. 7, 2016

(87) PCT Pub. No.: WO2015/094548
PCT Pub. Date: Jun. 25, 2015

(65) Prior Publication Data
US 2017/0022214 A1    Jan. 26, 2017

Related U.S. Application Data

(60) Provisional application No. 61/917,390, filed on Dec. 18, 2013, provisional application No. 61/918,810, filed on Dec. 20, 2013.

(51) Int. Cl.
*C07D 493/04*   (2006.01)

(52) U.S. Cl.
CPC .................................. *C07D 493/04* (2013.01)

(58) Field of Classification Search
CPC ...................................................... C07D 493/04
See application file for complete search history.

(56) References Cited

U.S. PATENT DOCUMENTS

2014/0088226 A1*   3/2014   Gevers ................. C07D 493/04
                                                                 524/109

\* cited by examiner

*Primary Examiner* — Timothy R Rozof
(74) *Attorney, Agent, or Firm* — William B. Miller

(57) ABSTRACT

A method for preparing esters from isohexide compounds, and a means by which color bodies that may be made in situ during esterification of isohexide compounds are either prevented from forming or their amounts are minimized in the resultant product mixture are described.

21 Claims, 6 Drawing Sheets

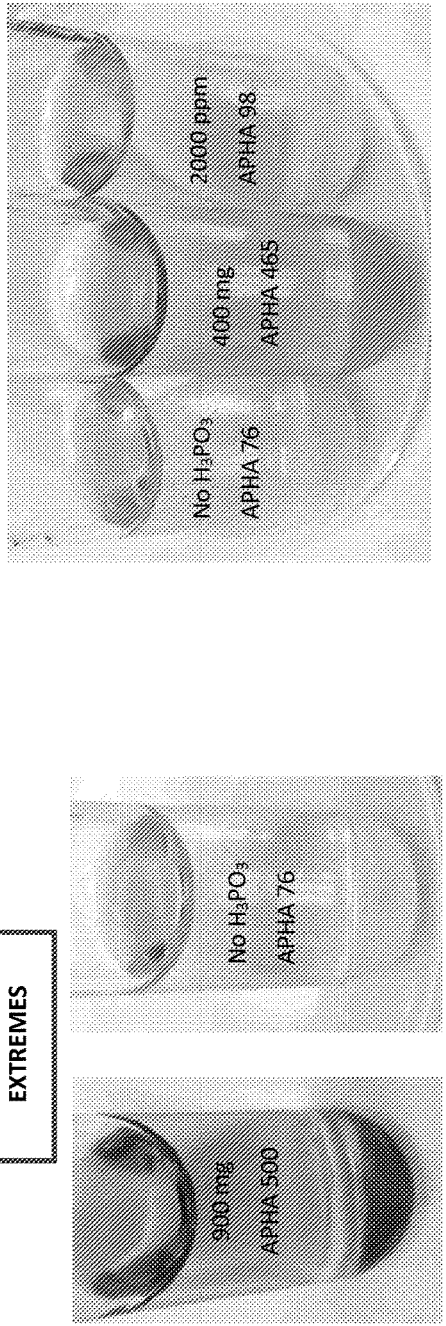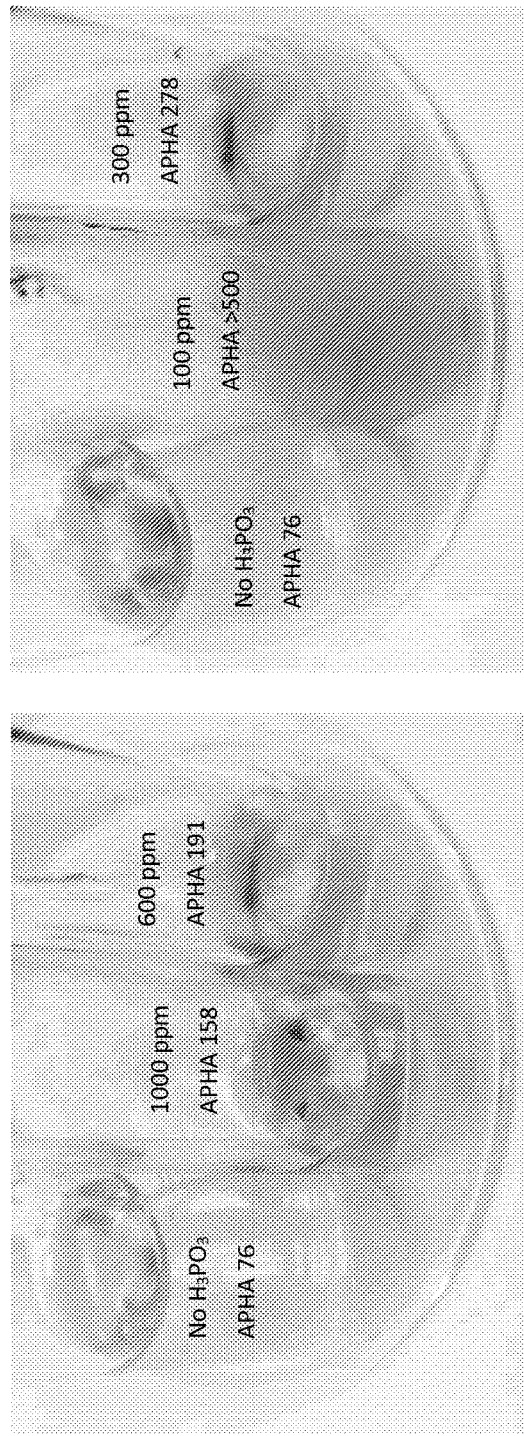
FIG. 6

CONTROL OF COLOR-BODY FORMATION IN ISOHEXIDE ESTERIFICATION

BENEFIT OF PRIORITY

The present application is a national stage entry of International Application No. PCT/US2014/066301, filed Nov. 19, 2014, which itself claims benefit of priority to U.S. Provisional Application Nos.: 61/917,390, filed on Dec. 18, 2013, and 61/918,810, filed Dec. 20, 2013, the contents of which are incorporated herein by reference.

FIELD OF INVENTION

The present disclosure relates to certain cyclic bi-functional materials that are useful as monomers in polymer synthesis, as well as plasticizers, surfactants and intermediate chemical compounds. In particular, the present invention pertains to esters of 1,4:3,6-dianhydrohexitols and methods for their preparation.

BACKGROUND

Traditionally, polymers and commodity chemicals have been prepared from petroleum-derived feedstock. As petroleum supplies have become increasingly costly and difficult to access, interest and research has increased to develop renewable or "green" alternative materials from biologically-derived sources for chemicals that will serve as commercially acceptable alternatives to conventional, petroleum-based or -derived counterparts, or for producing the same materials as produced from fossil, non-renewable sources.

One of the most abundant kinds of biologically-derived or renewable alternative feedstock for such materials is carbohydrates. Carbohydrates, however, are generally unsuited to current high temperature industrial processes. Compared to petroleum-based, hydrophobic aliphatic or aromatic feedstocks with a low degree of functionalization, carbohydrates such as sugars are complex, multi-functionalized hydrophilic materials. As a consequence, researchers have sought to produce biologically-based chemicals that can be derived from carbohydrates, but which are less highly functionalized, including more stable bi-functional compounds, such as 2,5-furandicarboxylic acid (FDCA), levulinic acid, and 1,4:3,6-dianhydrohexitols.

1,4:3,6-Dianhydrohexitols (also referred to herein as isohexides) are derived from renewable resources from cereal-based polysaccharides. Isohexides embody a class of bicyclic furanodiols that derive from the corresponding reduced sugar alcohols, for example depending on the chirality, D-sorbitol, D-mannitol, and D-iditol are dehydrated and cyclized to A) isosorbide, B) isomannide, and C) isoidide, respectively, the structures of which are illustrated in Scheme A.

Scheme A:

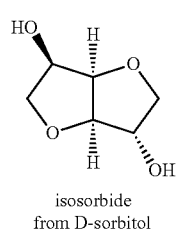

A isosorbide
from D-sorbitol

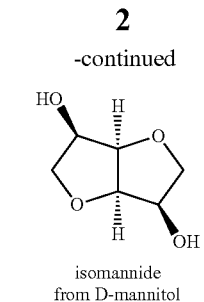

B isomannide
from D-mannitol

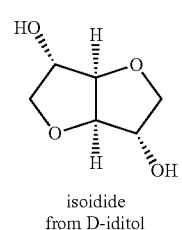

C isoidide
from D-iditol

These molecular entities have received considerable interest and are recognized as valuable, organic chemical scaffolds for a variety of reasons. Some beneficial attributes include relative facility of their preparation and purification, the inherent economy of the parent feedstocks used, owing not only to their renewable biomass origins, which affords great potential as surrogates for non-renewable petrochemicals, but perhaps most significantly the intrinsic chiral bi-functionalities that permit a virtually limitless expansion of derivatives to be designed and synthesized.

The isohexides are composed of two cis-fused tetrahydrofuran rings, nearly planar and V-shaped with a 120° angle between rings. The hydroxyl groups are situated at carbons 2 and 5 and positioned on either inside or outside the V-shaped molecule. They are designated, respectively, as endo or exo. Isoidide has two exo hydroxyl groups, while the hydroxyl groups are both endo in isomannide, and one exo and one endo hydroxyl group in isosorbide. The presence of the exo substituents increases the stability of the cycle to which it is attached. Also exo and endo groups exhibit different reactivities since they are more or less accessible depending on the steric requirements of the derivatizing reaction.

As interest in chemicals derived from natural resources increases, potential industrial applications have generated interest in the production and use of isohexides. For instance, in the field of polymeric materials, the industrial applications have included use of these diols to synthesize or modify polycondensates. Their attractive features as monomers are linked to their rigidity, chirality, non-toxicity, and the fact that they are not derived from petroleum. For these reasons, the synthesis of high glass transition temperature polymers with good thermo-mechanical resistance and/or with special optical properties is possible. Also the innocuous character of the molecules opens the possibility of applications in packaging or medical devices. For instance, production of isosorbide at a large industrial scale with a purity satisfying the requirements for polymer makers could be the basis for isosorbide to emerge as an important compound for industrial polymer applications. (See e.g., F. Fenouillot et al., "Polymers From Renewable 1,4:3,6-Dianhydrohexitols (Isosorbide, Isommanide and Isoidide): A Review," PROGRESS IN POLYMER SCIENCE, vol. 35, pp. 578-622 (2010); or X. Feng et al., "Sugar-based Chemicals for Environmentally sustainable Applications," CONTEMPORARY SCIENCE OF POLYMERIC MATERIALS, Am. Chem. Society, December 2010; or isosorbide-based plasticizers, e.g., U.S. Pat. No. 6,395,810, contents of each are incorporated herein by reference.)

One of the common disadvantages with the use of isohexides to make ester derivatives is the tendency of the synthesis reactions to generate color-bodies as a side product or as a degradation of byproduct compounds derived from reacting the isohexides. Typically, the color-bodies are formed at elevated temperatures, in the presence of oxygen. Given that esters manifest a multitude of utilities as plasticizers, dispersants, lubricants, flavoring agents, solvents, etc., and that isohexide esters are commonly used as plasticizers and polymers, and variants thereof are being aggressively synthesized and studied for enhanced performance in these realms vis a vis current materials, better process to synthesize product of greater purity with less color-bodies is desirable. A way to reduce the formation of color-bodies would help manufacturers produce a better quality and purer final product.

SUMMARY OF INVENTION

The present disclosure relates, in part, to a method for preparing esters from isohexide ester. Generally, the method involves reacting an isohexide and an organic acid, in the presence of a reducing Brønsted acid catalyst at a temperature up to about 250° C., for a time sufficient to produce the isohexide ester while limiting formation of color bodies in a product mixture to an APHA value of less than 230. The method further includes reducing incumbent color bodies or color-generating precursor compounds in a preparation of the isohexide or organic acid prior to esterification with the reducing Brønsted acid catalyst.

Additional features and advantages of the present purification process will be disclosed in the following detailed description. It is understood that both the foregoing summary and the following detailed description and examples are merely representative of the invention, and are intended to provide an overview for understanding the invention as claimed.

BRIEF DESCRIPTION OF FIGURES

FIG. 6, are photos of the results of a high temperature thermal stress tests for about 10 g. of isosorbide product mixture, which was subjected to 200° C. for 1 hour in air.

DETAILED DESCRIPTION OF THE INVENTION

Section I.—Description

Figure 1:
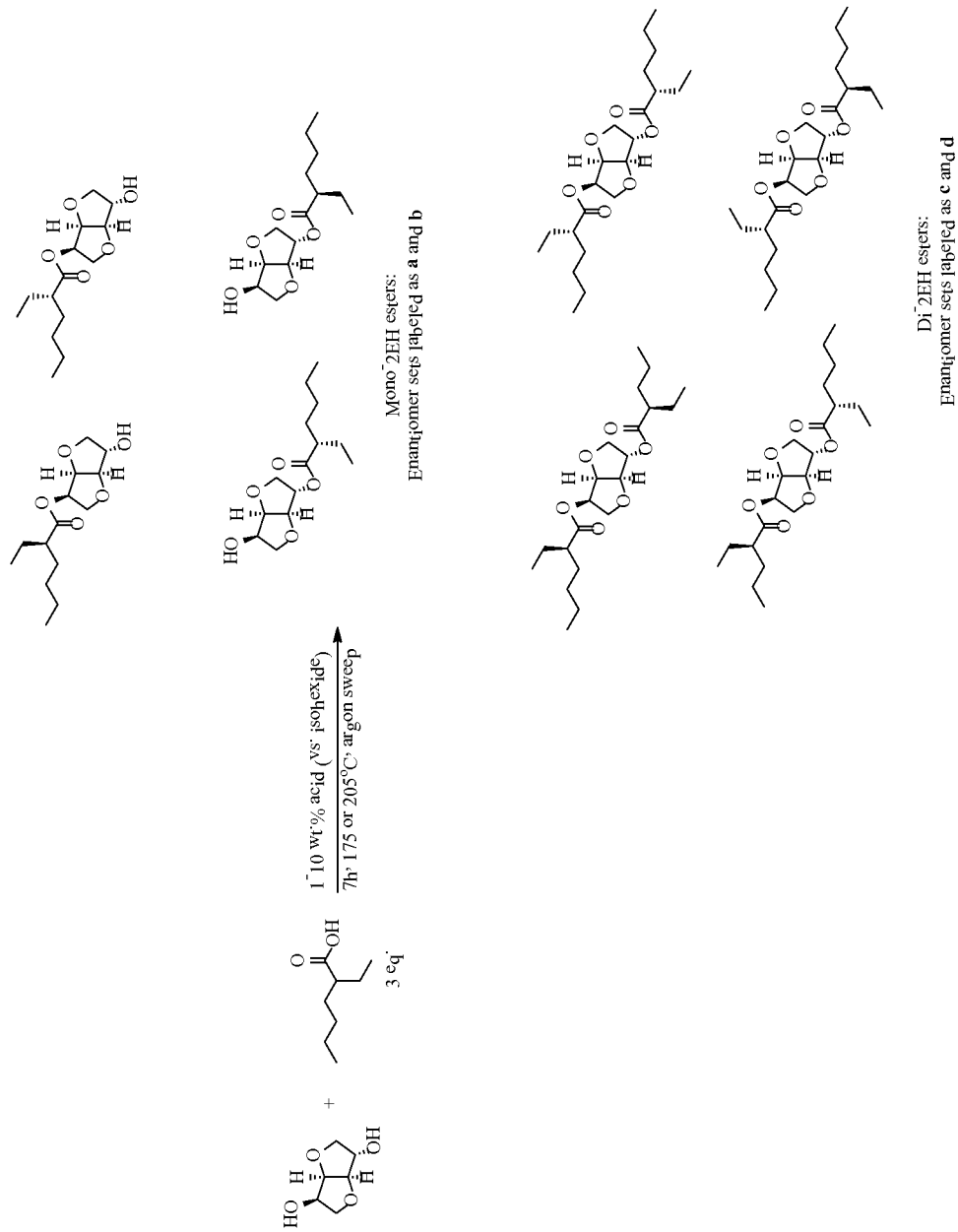
FIG. 1, depicts an exemplary synthesis of isosorbide esters according to an embodiment of the present method.

As biomass derived compounds that afford great potential as surrogates for non-renewable petrochemicals, 1,4:3,6-dianhydrohexitols are a class of bicyclic furanodiols that are valued as renewable molecular entities. (For sake of convenience, 1,4:3,6-dianhydrohexitols will be referred to as "isohexides" in the Description hereinafter.) As referred to above, the isohexides are good chemical platforms that have recently received interest because of their intrinsic chiral bi-functionalities, which can permit a significant expansion of both existing and new derivative compounds that can be synthesized.

Isohexide starting materials can be obtained by known methods of making respectively isosorbide, isomannide, or isoidide. Isosorbide and isomannide can be derived from the dehydration of the corresponding sugar alcohols, D-sorbitol and D mannitol. As a commercial product, isosorbide is also available easily from a manufacturer. The third isomer, isoidide, can be produced from L-idose, which rarely exists in nature and cannot be extracted from vegetal biomass. For this reason, researchers have been actively exploring different synthesis methodologies for isoidide. For example, the isoidide starting material can be prepared by epimerization from isosorbide. In L. W. Wright, J. D. Brandner, *J. Org. Chem.*, 1964, 29 (10), pp. 2979-2982, epimerization is induced by means of Ni catalysis, using nickel supported on diatomaceous earth. The reaction is conducted under relatively severe conditions, such as a temperature of 220° C. to 240° C. at a pressure of 150 atmosphere. The reaction reaches a steady state after about two hours, with an equilibrium mixture containing isoidide (57-60%), isosorbide (30-36%) and isomannide (5-7-8%). Comparable results were obtained when starting from isoidide or isomannide. Increasing the pH to 10-11 was found to have an accelerating effect, as well as increasing the temperature and nickel catalyst concentration. A similar disclosure can be found in U.S. Pat. No. 3,023,223, which proposes to isomerize isosorbide or isomannide. More recently, P. Fuertes proposed a method for obtaining L-iditol (precursor for isoidide), by chromatographic fractionation of mixtures of L-iditol and L-sorbose (U.S. Patent Publication No. 2006/0096588; U.S. Pat. No. 7,674,381 B2). L-iditol is prepared starting from sorbitol. In a first step sorbitol is converted by fermentation into L-sorbose, which is subsequently hydrogenated into a mixture of D-sorbitol and L-iditol. This mixture is then converted into a mixture of L-iditol and L-sorbose. After separation from the L-sorbose, the L-iditol can be converted into isoidide. Thus, sorbitol is converted into isoidide in a four-step reaction, in a yield of about 50%. (See, e.g., International Patent Application WO13125950) The contents of the cited references are incorporated herein by reference.

A. Preparation of Isohexide Esters

Fischer-Speier esterification is the current standard protocol for industrial preparation of esters. Fischer-Speier esterification embodies a straightforward process for direct alcohol acylation with carboxylic acids employing Brønsted or Lewis acid catalysts. However, color is problematic when converting thermally sensitive substrates such as isohexides in the presence of strong acid catalysts. The desire is to minimize downstream processing unit operations by developing a catalyst that can furnish relatively high yields (e.g., ≥55%-60%) of target esters while minimizing color body formation or accretion.

In contrast to conventional commercial esterification protocols, which typically involve at least two operational steps a synthesis reaction followed with purification or decolorization (e.g., crystallization, distillation and/or chromatography) of the product the esterification method according to the present invention is simpler. The method involves a single-step operation. In the commercial realm, there is a desire to eliminate downstream processing entirely. Hence, a process that can make either product which is or approaches colorlessness (so-called "water-white"), or product that is within tolerable color specifications, in a single reaction without further need for later purification would be quite advantageous in terms of cost and efficiency.

For purposes of ascertaining acceptable levels of color in the product mixture, one employs the APHA color standard, named for the American Public Health Association and defined by ASTM D1209, incorporated herein by reference. (It was originally intended to describe the color of waste water, but its usage has expanded to include other industrial applications.) APHA is similar to the Hazen color scale test, which uses a platinum-cobalt (Pt/Co) solution, where the color of water could be used as a measure of concentration of dissolved and particulate material. Impurities can be deeply colored, for instance dissolved organic compounds such as tannins can result in dark brown colors. The APHA color scale is from 0 to 500, where 0 is colorless and 500 is the most colored.

A feature of the present invention is the ability to reduce or eliminate color bodies that may be made in situ during esterification of an isohexide compound. The color bodies are either prevented from forming or their amounts are minimized in the resultant product mixture. The method involves: reacting an isohexide and a carboxylic acid, in the presence of a reducing Brønsted acid catalyst for a time sufficient to yield a product mixture that exhibits an APHA value of less than 230. Typically, the product mixture exhibits an APHA value of ≤185, desirably the APHA value is ≤150.

The isohexide can be at least one of: isosorbide, isomannide, and isoiodide. The organic acid can be at least an alkanoic acid, alkenoic acid, alkynoic and aromatic acid, having $C_2$-$C_{26}$. The isohexide is transformed to a corresponding ester at a conversion rate of at least 40%, desirably the conversion rate is about 50% or greater.

The esterification is performed at a temperature in a range from about 150° C. or 160° C. to about 240° C. or 250° C. Typically, the reaction temperature is in a range from about 170° C. or 175° C. to about 205° C. or 220° C.

The reducing Brønsted acid catalyst is present in an amount of at least 0.5 wt. % relative to the amount of isohexide. In certain embodiments, when the amount of reducing Brønsted acid catalyst is >5.0 wt. %, the product mixture contains predominantly diesters. In other embodiments, when the reducing Brønsted acid catalyst is present in an amount from about 2.5 wt. % to about 5.0 wt. %, the product mixture contains about a 1:1 ratio of monoesters and diesters. In still other embodiments, when the amount of reducing Brønsted acid catalyst is present in an amount <2.5 wt. %, the product mixture contains predominantly monoesters.

Table 1, lists several conventional acid catalyst species that have commercial or potential value as comparative examples in terms of product color, catalyst load, and conversion rate relative to a reducing Brønsted acid. The methods described herein are exemplified by use of phosphonic acid ($H_3PO_3$) also known as phosphorus acid as the reducing Brønsted acid. In Table 1, the comparative examples tended to generate dark colored products with APHA values over 250.

TABLE 1

Catalyst, Catalyst Load, Percent (%) Isosorbide conversion, APHA Color Values

| Catalyst | Loading (wt. % vs. isosorbide) | APHA | % isosorbide conversion |
|---|---|---|---|
| Autocatalysis | 0.0 | 500 | 23.39 |
| Sn(II)2EH | 9.9 | 500 | 66.23 |
| Sn(II)2EH | 5.1 | 500 | 42.11 |
| (butyl)$_2$SnCl$_2$ | 5.2 | 500 | 38.66 |
| HaCl$_4$ | 5.4 | 500 | 52.83 |
| (butyl)$_2$Sn(laurate)$_2$ | 5.1 | 306 | 35.28 |
| ZrCl$_4$ | 5.4 | 500 | 42.16 |
| ZrCl$_4$ | 5.1 | 500 | 47.98 |
| (butyl)$_2$Sn(maleate) | 5.3 | 319 | 38.48 |
| SnCl$_4$ | 5.7 | 500 | 88.55 |
| SnCl$_2$ | 5.7 | 277 | 87.99 |
| BiCl$_3$ | 5.7 | 500 | 36.33 |
| La(OTf)$_3$ | 1.0 | 500 | 82.49 |
| Dibutyltin(IV)oxide | 5.7 | 281 | 31.88 |
| Fe(OTf)$_3$ | 1.0 | 500 | 69.91 |
| Pre-reaction mixture | | 96 | |
| Phosphorus acid | 11.6 | 131 | 93.99 |
| Phosphorus acid | 6.7 | 145 | 83.73 |
| Phosphorus acid | 4.9 | 153 | 74.08 |
| Phosphorus acid | 3.6 | 168 | 58.79 |
| Phosphorus acid | 1.3 | 180 | 40.92 |
| Phosphorus acid | 0.6 | 196 | 28.43 |

Certain strong Brønsted or Lewis acid catalysts (e.g., $H_2SO_4$) will produce color-bodies. We have found that inclusion of a reducing Brønsted acid and one or more Brønsted and/or Lewis acid that effectuates high conversion of isosorbide to the corresponding mono and diesters of 2-ethylhexanoic acid can also concomitantly mitigate the buildup of colored bodies in the product. The color tincture of the product mixture of the esterification decreases with an increase in concentration of the reducing Brønsted acid catalyst.

A particular reducing Brønsted acid species is phosphonic acid ($H_3PO_3$), also known as phosphorus acid, which is a crystalline solid, commercially available, inexpensive, and possesses a strong acidity (pKa~1). This material evinces both high catalytic activity in the context of Fischer esterifications and pronounced color attenuation of the product mixture. To date, we believe that phosphonic acid has not received significant attention in this regard, either as a Brønsted acid in the catalysis of isohexide acylation with carboxylic acids, concerning color mitigation of products or concerning high isohexide conversions. Further, at this time, phosphonic acid is one that manifests both high reactivity and concomitant color diminution.

Hence, it was surprising to discover that, although a Brønsted acid, phosphonic acid not only helps to catalyze and increase the conversion rate to make esters from isohexides, but also can help reduce significantly the development of undesired color bodies in the product mixture when used in sufficient quantities (e.g., ≥1.0 wt. %; preferably ≥1.5 wt. % or 2.0 wt. %). Phosphonic acid manifests highly effective catalytic activity (~80%-95%) (i.e., efficacy similar to that exhibited for tin chlorides, ~87%-89%), in the esterification of isosorbide to mono and diesters of 2-ethylhexanoic acid, according to a particular embodiment.

Phosphonic acid proved to yield high isosorbide conversion to the corresponding mono- and diesters, while also displaying pronounced antioxidant properties that effectively controls and inhibits color body formation or accumulation in the product mixture.

Phosphonic acid functions as a catalyst for the acylation reaction, as well as provides a powerful reducing agent in solution that helps mitigate the formation of color bodies. Although not to be bound by theory, it is believed that the phosphonic acid may interact with color-body precursors to prevent their transition to colored entities. Scheme 1 illustrates one embodiment of the reaction. The reaction is performed neat.

Scheme 1. Phosphonic acid ($H_3PO_3$) catalyzed Fischer esterification of isosorbide to mono- and diesters of 2-ethylhexanoic acid (2EH).

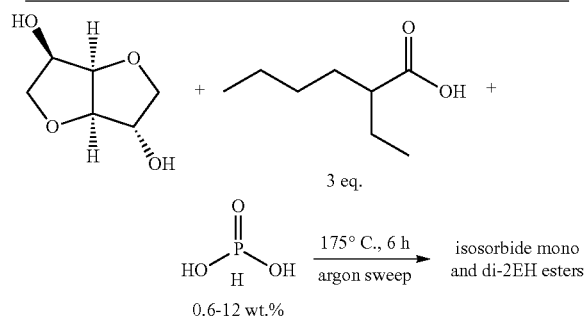

According to the present method, the conversion rate of isohexide to its corresponding esters is about least 40%-50%. Typically, the isohexide conversion rate is about 55% or greater, more typically about 65% or 70% or greater (e.g., about 75%, 80%, 84%, 87%, 90%, 92%, 95%, or greater).

While the method described herein are exemplified with 2-ethylhexanoic acid, the method is suitable for use with any organic acid desired for esterification with the isohexide, including alkanoic acid, alkenoic, and aromatic acids of $C_2$ to $C_{26}$ in size, provided only that the organic acid is soluble in the reaction mixture.

Phosphonic acid is reported to decompose to phosphoric acid and phosphine at 200° C., and yet doesn't seem to adversely affect the esterification process/color body mitigation at this temperature, as demonstrated by results in Table 2, where isosorbide manifested complete conversion to the corresponding esters, primarily diesters, with minimal color accretion from reactions carried out at 205° C. for 7 h.

TABLE 2

$H_3PO_3$ Catalyzed Isosorbide Esterification with Distilled 2-Ethyl-Hexanoic Acid (2EH), 205° C., 7 h.

| Sample | Comparison | Loading (wt. % vs. isosorbide) | APHA (color) | % isosorbide conversion |
|---|---|---|---|---|
| 1. | Pre-reaction mixture undistilled 2EH | | 96 | |
| 2. | Pre-reaction mixture distilled 2EH | | 6 | |
| 3. | Auto-catalysis | 0 | 263 | 57 @ 5 h |
| 4. | Phosphonic Acid | 1.20 | 136-138 | 85 @ 5 h |
| 5. | Phosphonic Acid | 5.48 | 98 | 100 @ 5 h |

As part of the process to minimize color, one can either pre-purify the staring reagents, for example, by distilling the alkanoic acid (also may use alkenoic or alkynoic acids) before esterification or perform follow-on chromatography, among other purification techniques. The result of using phosphonic acid in the product mixture at a concentration of about 1 wt. % (APHA 136-138) and 5 wt. % (APHA 98), respectively, manifests relatively good color attenuation in comparison to the auto-catalysis value (APHA 263), and was much more closer in color to that of the clear distilled 2EH solution (APHA 6).

A unique feature of phosphonic acid is that it not only catalyzes the reaction, but has propitious reducing agent potential, and thus can further oxidize to phosphoric acid. In the area of isohexide esterification, phosphonic acid is the only catalyst of those screened to date, that discerns both high isosorbide conversion and color mitigation. Furthermore, no literature precedent for such behavior (aggressive catalysis, color mediation) was distinguished.

Others have used hypophosphorus acid ($H_3PO_2$), an aqueous solution. The kinetics of the reaction may be similar to that of the hypophosphorus and phosphonic acid as each has pKa near 1. Comparative catalyses for these acids, however, suggest that the chemistry that each of the acids display in mitigating color are likely dissimilar. Hypophosphorus acid degrades at 130° C., and can be obtained only as a 50% aqueous solution, which because of the presence of water would not function in a similar manner as phosphonic acid in the present reaction system.

As an exemplary method, the present synthesis protocol for acid-catalyzed esterification of isohexides (e.g., isosorbide) with an carboxylic acid (e.g., 2-ethylhexanoic acid) involves: A three-neck, 500 mL round bottomed flask equipped with a tapered, PTFE coated magnetic stir bar is charged with 50 g of isosorbide (0.342 mol), 148 g of 2-ethylhexanoic acid (1.026 mol) and 5 wt. % acid catalyst (relative to isosorbide). The necks of the flask are fitted with a Dean-Stark trap, argon line, and a rubber septum centrally pierced by a stainless steel thermocouple. The flask is immersed in an oil bath and heated to 175° C. with a concurrent, vigorous argon sweep. Aliquots are pulled each hour and analyzed by gas chromatography. The reaction is halted at 7 hours. FIG. 1 illustrates an embodiment of the present method for synthesizing isosorbide 2EH monoesters.

Figure 2:
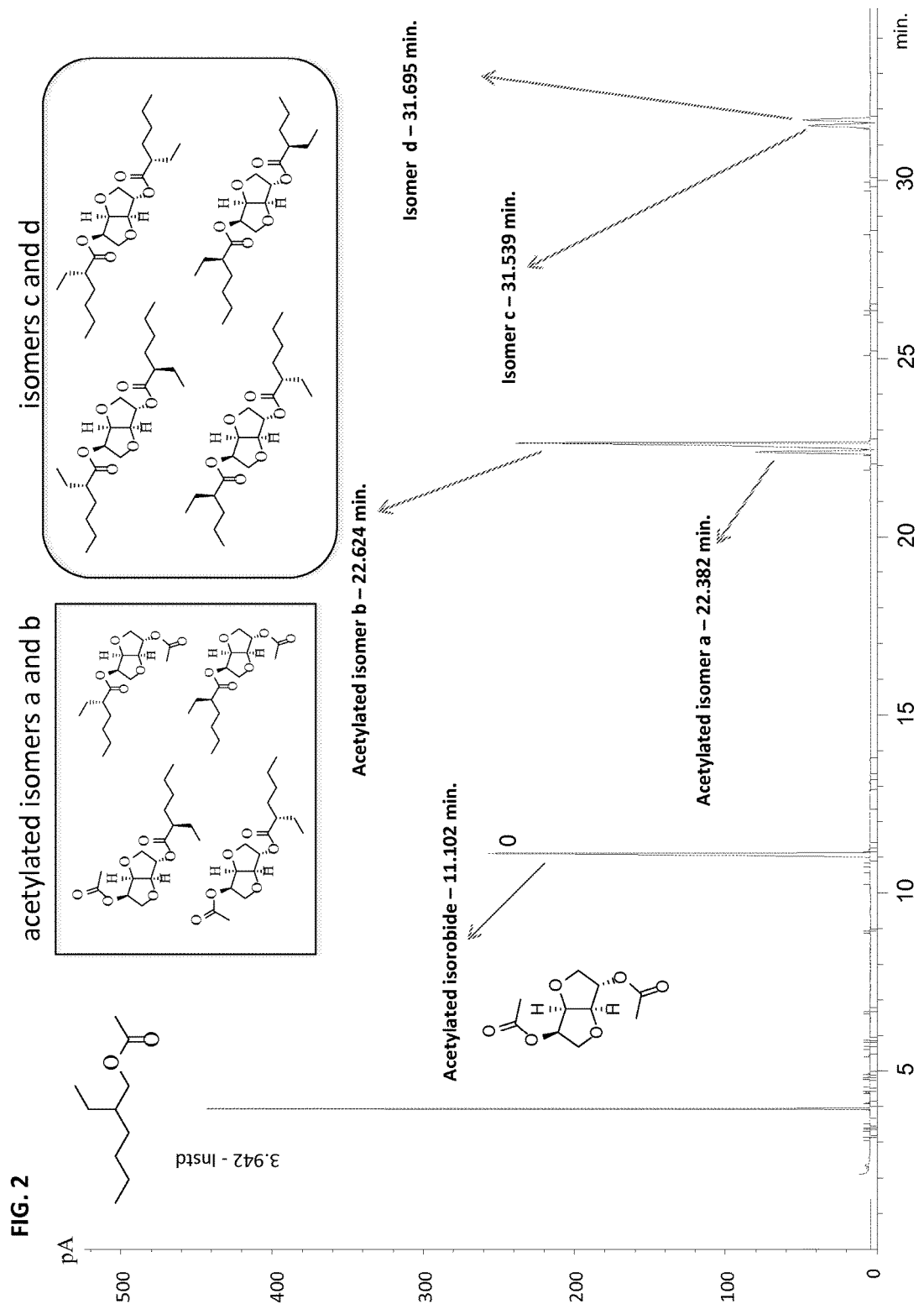
FIG. 2, shows a chromatogram of results obtained from quantitative analysis conducted by gas chromatography (GC) of isomers synthesized according to an embodiment of the present invention.

FIG. 2, is a representative chromatogram of the results obtained from quantitative analysis conducted by gas chromatography (GC) of the two sets of four isomers synthesized according to the reaction above.

Figure 3:
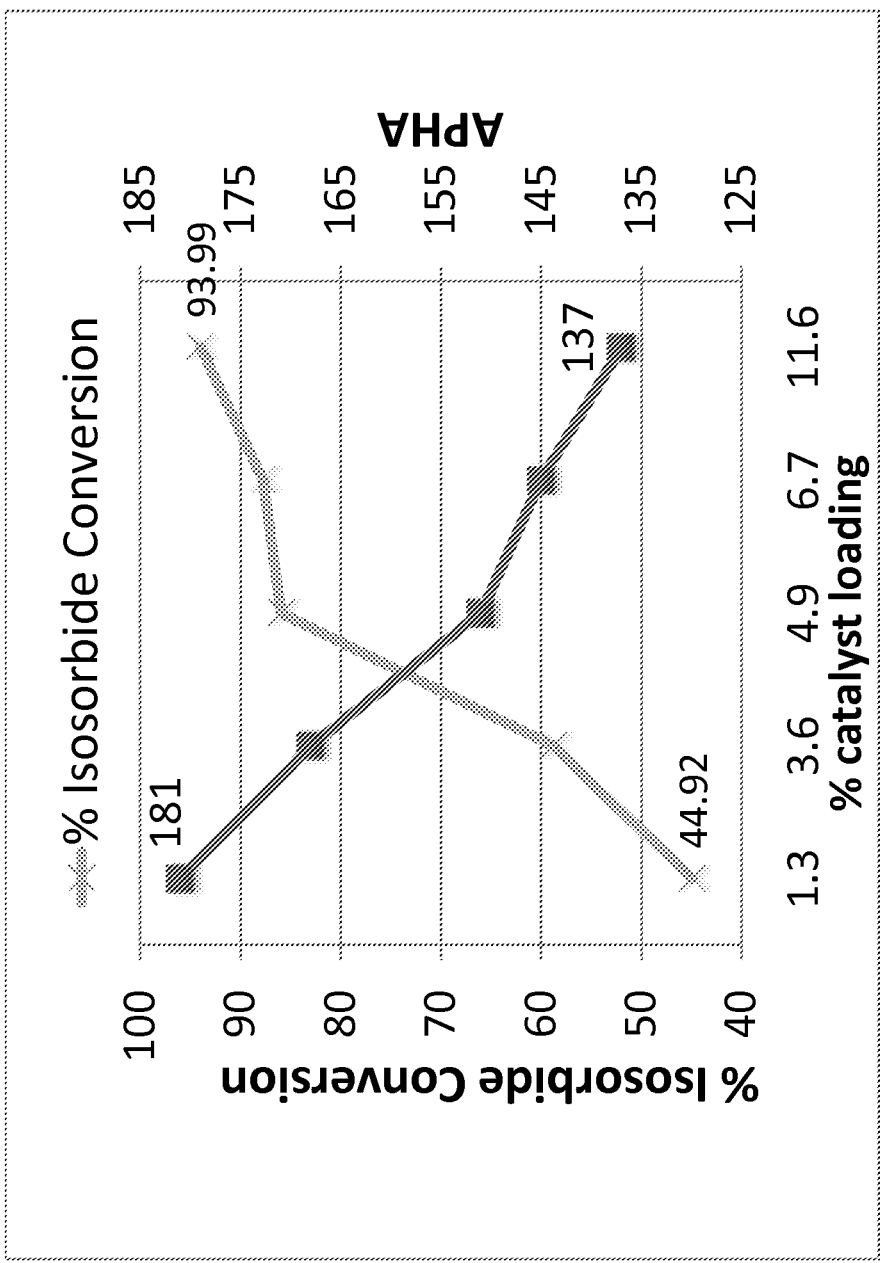
FIG. 3, is a graph showing the relationship between the percent catalyst load of phosphonic acid ($H_3PO_3$) and its impact on APHA values and percent conversion of isosorbide when reacted at 175° C., 7 hours.

Interplay of three factors—catalyst load, temperature, and time appears to facilitate the operation of the esterification reaction to yield low amounts of color bodies, which leads to a clearer product and minimizes a need for downstream purifications. Counterintuitive to conventional observations in which an acid catalyst at greater amounts tend to generate more color bodies, one of the advantages and unexpected results of using phosphonic acid is that as the catalyst load of acid increases manifestation of color-bodies tends to decrease. FIG. 3, is a graph showing the relationship between the percent catalyst load of phosphonic acid ($H_3PO_3$) and its impact on APHA values and percent conversion of isosorbide when reacted at 175° C., 7 hours. As the acid catalyst concentration increases from 1.3 wt. % to 11.6 wt. %, the APHA color value of the product mixture decreases from 181 to 137, and the conversion rate increases from about 45% to about 94%.

Figure 4:
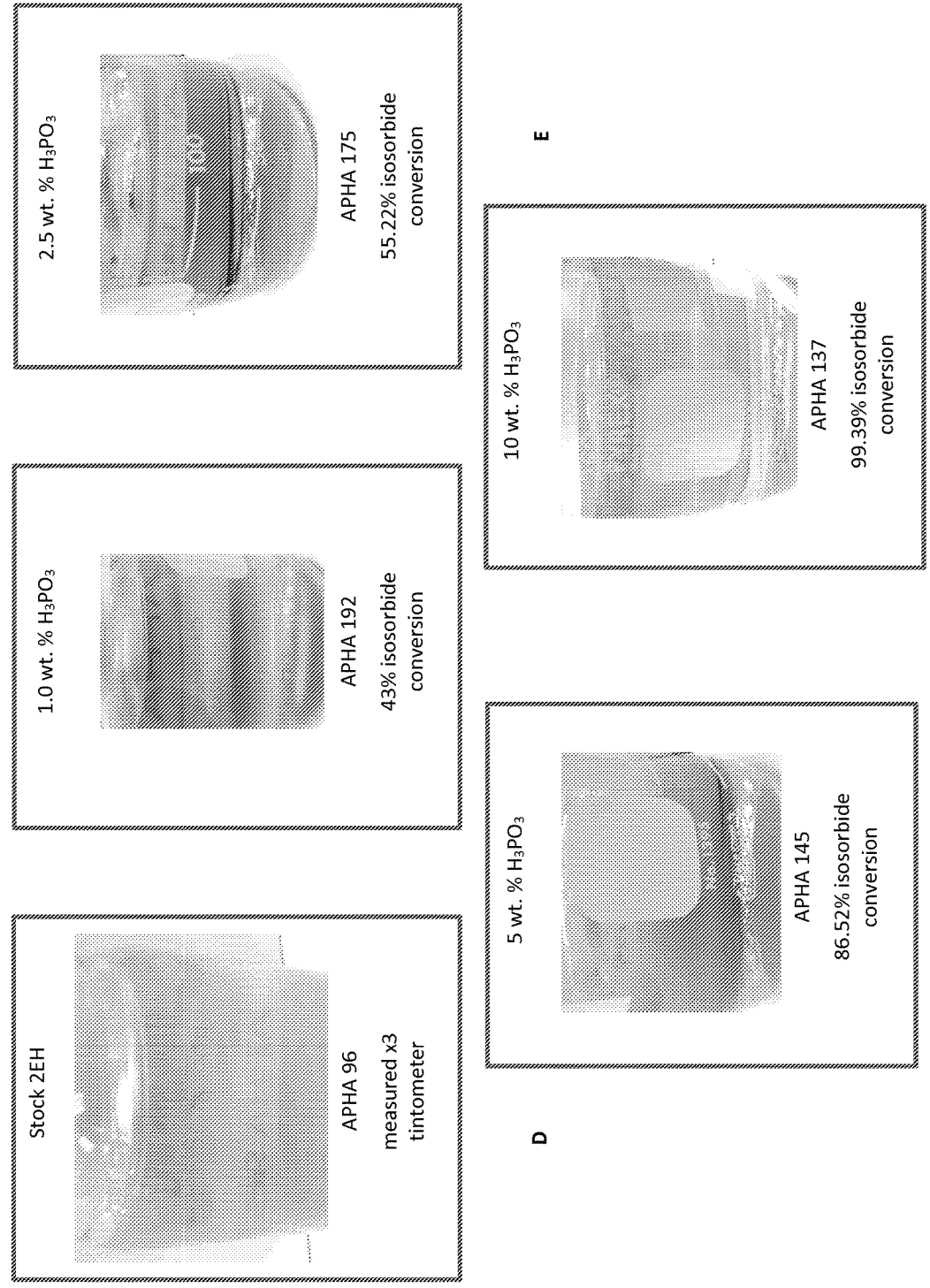
FIG. 4, shows a series of photos of the respective degree of color attenuation in isohexide ester product mixtures that have been reacted with $H_3PO_3$ catalyst (175° C., 7 h.), as compared to stock solution of 2-ethyl-hexanoic acid (2EH).

FIG. 4, shows several photos of isosorbide product that have undergone acylation according to the present process. The accompanying photos highlight the dual role catalytic and oxygen scavenging effect of phosphonic acid. In comparison to the stock 2-ethylhyexanoic acid A, with APHA tintometer value of 96, product mixture samples reacted (at 175° C. for 7 h) with phosphonic acid at 1 wt. % B, 2.5 wt. % C, 5 wt. % D, and 10 wt. % E catalyst load, respectively, show decreased color (APHA value of 192, 175, 145, and 137, respectively), while increased conversion yields of isosorbide from 43.56%, 55.22%, 86.52%, to 99.39%, respectively. In other words, with greater amounts of catalysts one can achieve greater yield or conversion of the isohexide while still maintaining a clear solution with good color quality with APHA value of less than about 200. Test results for this phenomenon are summarized in Tables 1 and 3, which were reacted at 205° C. and 175° C., respectively, for 7 hours.

TABLE 3

$H_3PO_3$ Catalysis Results: 2-Ethyl-Hexanoic Acid Esterification with Isosorbide, 175° C., 7 h.

| Sample | Loading (wt. % vs. isosorbide) | APHA (color) | % Isosorbide conversion | Exo/Endo (mean) | Exo/Endo (std. dev) | % CV |
|---|---|---|---|---|---|---|
| 1. Comp. | 0 | 96 | | | | |
| 2. | 11.6 | 137 | 93.99 | 4.05 | 0.07 | 1.59 |
| 3. | 6.7 | 145 | 87.73 | 3.95 | 0.08 | 2.02 |
| 4. | 4.9 | 151 | 85.92 | 4.09 | 0.08 | 2.02 |
| 5. | 3.6 | 168 | 58.79 | 4.02 | 0.10 | 2.37 |
| 6. | 1.3 | 181 | 44.92 | 3.96 | 0.08 | 2.00 |

N.B.: Product mixture from samples of catalysts typically used manifest APHA >275.

Additionally, as results in Table 3, suggest that phosphonic acid exhibits greater regioselectivity for the exo-OH over the endo-OH of an isohexide molecule in a ratio of about 4:1.

Figure 5:
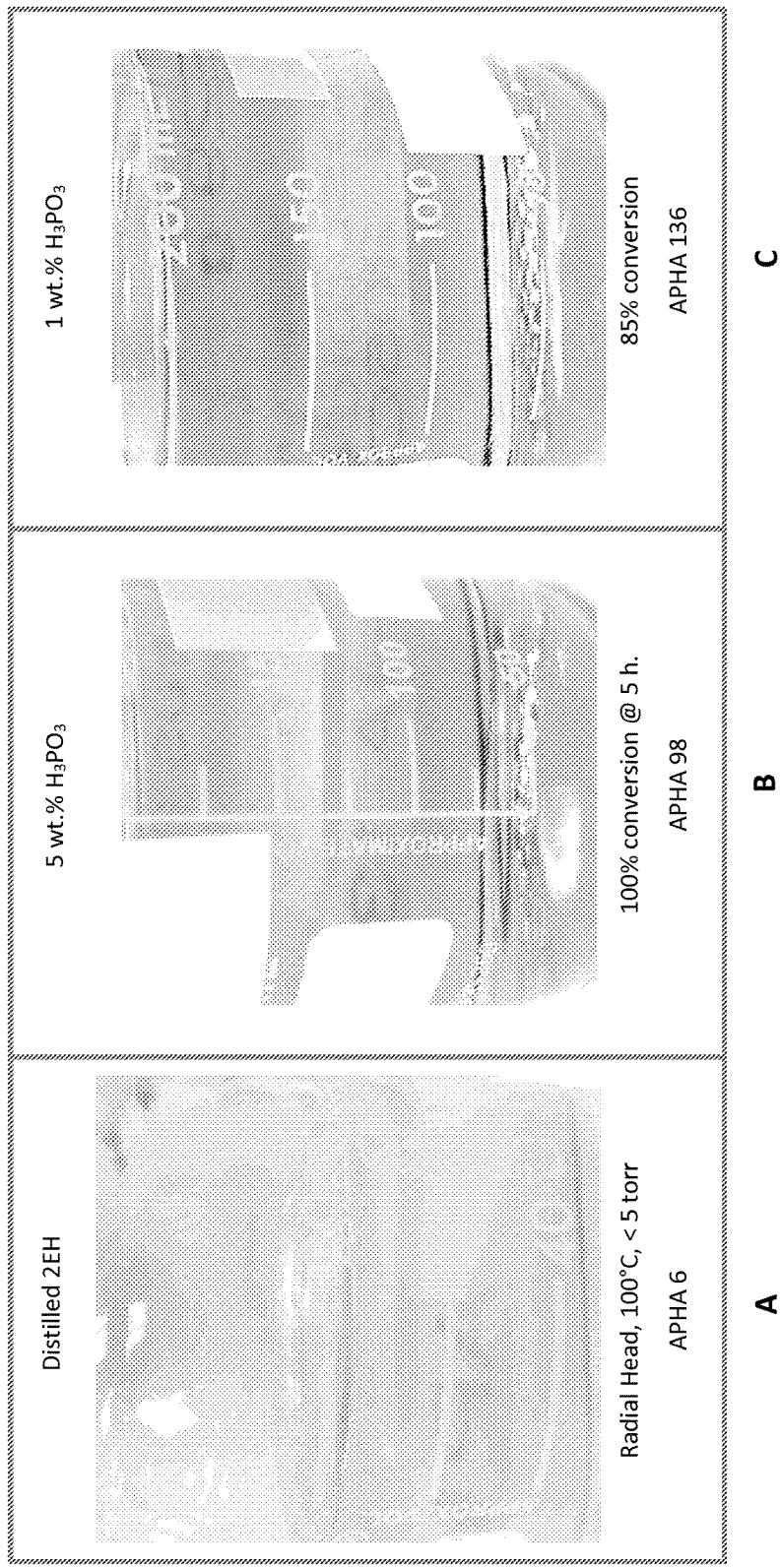
FIG. 5, shows photos of APHA color attenuation in isohexide product mixtures prepared from a pre-distilled solution of 2EH (APHA 6) using phosphonic acid catalyst loads of 1 wt. % and 5 wt. %, respectively at 205° C., 7 hours.

FIG. 5, are photos that show the decrease in APHA color value in isohexide product mixtures associated with an increase in phosphonic acid catalyst load of 1 wt. % and 5 wt. %, respectively (APHA 136, 98), as compared to a pre-distilled solution of 2EH (APHA 6) at 205° C., 7 hours.

FIG. 6, shows photos of the results of high temperature thermal stress tests to explore the oxygen scavenging potential of the acid catalyst for mitigating color. The test sample contains about 10 g. of isosorbide product mixture, which was subjected to 200° C. for 1 hour in air. The results suggest a window of good oxygen-scavenging performance and/or ability to incapacitate colored body precursors generated from thermal oxidative decomposition of isosorbide in terms of the amount of phosphonic acid added to the isosorbide mixture. An isosorbide product sample that contains no phosphonic acid exhibits very light clear color (APHA~76), while at phosphonic acid amounts of about 90,000 ppm (900 mg) the solution exhibits a deep dark color (APHA 500). At phosphonic acid loads of about 100 ppm, 300 ppm, 1000 ppm, respectively, the color of the solution lightens with increasing concentration (APHA>500, 278, 191, 158, respectively). However, at a concentration of about 40,000 ppm (400 mg), the color of the solution darkens (APHA 465) again. This suggests that the window has a lower and upper limit for the amount of phosphonic acid between about 2,000 ppm (0.2 wt. %) (APHA 98) to about 5,000 ppm (0.5 wt. %) or about 10,000 ppm (1.0 wt. %) that is effective at maintaining control of color body development to a relatively low level, at an APHA value between about 76 and about 105.

TABLE 4

Phosphonic Acid-Catalyzed Esterification of Isohexides with 2-Ethyl-Hexanoic Acid

| Isohexide | Catalyst Loading (wt. % v. isohexide) | APHA (neat, tintometer) | Percent (%) isohexide conversion |
|---|---|---|---|
| Isosorbide | 4.9 | 151 | 85.92 |
| Isomannide | 5.3 | 210 | 75.27 |
| Isoiodide* | 5.2 | 187 | 99.69 |

*~80% purity, THF saturated

With regard to the three particular isohexides presented in Table 4, isosorbide (APHA 151) shows the best performance when reacted using phosphonic acid catalyst, with better color attenuation relative to either isoiodide (APHA187) or isomannide (APHA 210). This may be a result of the nature of isomannide and isoidide. Isomannide is much more thermo-oxidatively unstable than isososorbide. Nonetheless, an APHA value of 210 for isomannide is far lower color production than typical. Normally, when isomannide is esterified with conventional catalyst the product would manifest an APHA color value of well over 500. In another example, isomannide reacts with 7.6 wt. % phosphonic acid (vs. isomannide), and yields 89.44% isomannide conversion over 7 hours at 175° C. (APHA 210). The particular isoiodide sample shown in the Table is about 80% pure, containing a significant amount of THF, which is a species that is readily susceptible to thermo-oxidative decomposition, and hence generation of color bodies. We believe that for an isoiodide sample of greater purity (e.g., near 100% purity) one will see a greater reduction in color than that indicated. The isoiodide product would have coloration comparable to or better than that of the isosorbide sample.

Polyesters can be made from the isohexide esters (e.g., isosorbide esters) having an APHA value of ≤150 prepared according to the present method. Hence, one can employ a method of making a polyester by obtaining an isohexide ester monomer made according to the methods described herein, and polymerizing said isohexide ester monomer alone or with an additional monomer.

The present invention has been described in general and in detail by way of examples. Persons of skill in the art understand that the invention is not limited necessarily to the embodiments specifically disclosed, but that modifications and variations may be made without departing from the scope of the invention as defined by the following claims or their equivalents, including other equivalent components presently known, or to be developed, which may be used within the scope of the present invention. Therefore, unless changes otherwise depart from the scope of the invention, the changes should be construed as being included herein.

We claim:

1. A method for preparing an isohexide ester, comprising: reacting an isohexide and an organic acid, in the presence of a phosphonic acid ($H_3PO_3$) catalyst at a temperature from 150 degrees Celsius up to 250 degrees Celsius for a time sufficient to produce the isohexide ester while limiting formation of color bodies in a product mixture to an APHA value of less than 230.

2. The method according to claim 1, further comprising reducing color bodies or color-generating precursor compounds in a preparation of said isohexide or organic acid prior to esterification.

3. The method according to claim 2, wherein reducing color bodies or precursor compounds involves purifying the organic acid by at least one of chromatography, crystallization, or distillation.

4. The method according to claim 1, wherein said product mixture exhibits an APHA value of ≤185.

5. The method according to claim 1, wherein said product mixture exhibits an APHA value of ≤150.

6. The method according to claim 1, wherein said isohexide is transformed to said isohexide ester at a conversion rate of at least 40%.

7. The method according to claim 6, wherein said conversion rate is about 50% or greater.

8. The method according to claim 6, wherein said conversion rate is about 70% or greater.

9. The method according claim 1, wherein said isohexide is at least one of: isosorbide, isomannide, and isoiodide.

10. The method according to claim 1, wherein said organic acid is at least one of an alkanoic acid, alkenoic acid, or aromatic acid, having $C_2$-$C_{26}$.

11. The method according to claim 10, wherein said acid is 2-ethylhexanoic acid.

12. The method according to claim 1, wherein said phosphonic acid catalyst is present in an amount >5.0 wt. % of a reaction mixture of said isohexide and organic acid.

13. The method according to claim 1, wherein said phosphonic acid catalyst is present in an amount from about 2.5 wt. % to about 5.0 wt. % of a reaction mixture of said isohexide and organic acid.

14. The method according to claim 1, wherein said phosphonic acid catalyst is present in an amount <2.5 wt. % of a reaction mixture of said isohexide and organic acid.

15. The method according to claim 12, wherein said product mixture contains predominantly diesters.

16. The method according to claim 13, wherein said product mixture contains about a 1:1 ratio of monoesters and diesters.

17. The method according to claim 14, wherein said product mixture contains predominantly monoesters.

18. An ester product mixture comprising an isohexide ester prepared from an isohexide and an organic acid, in the presence of a reducing Brønsted acid catalyst, wherein said ester product mixture exhibits an APHA value of less than 230, and may contain said reducing Brønsted acid.

19. The ester product mixture formed according to claim 18, wherein said APHA value is ≤180.

20. The ester product mixture formed according to claim 18, wherein said reducing Brønsted acid catalyst is phosphonic acid ($H_3PO_3$).

21. A method of making a polyester comprising, obtaining an isohexide ester monomer according to claim 1 or in the ester product mixture of claim 18, and polymerizing said isohexide ester monomer either alone with itself or with at least an additional other monomer.

* * * * *